US012196743B2

United States Patent
Hattori et al.

(10) Patent No.: US 12,196,743 B2
(45) Date of Patent: Jan. 14, 2025

(54) METHOD FOR ANALYZING GLYCOSAMINOGLYCAN

(71) Applicants: SHIMADZU CORPORATION, Kyoto (JP); NATIONAL UNIVERSITY CORPORATION SHIMANE UNIVERSITY, Matsue (JP)

(72) Inventors: Takanari Hattori, Kyoto (JP); Jun Watanabe, Kyoto (JP); Tetsuo Iida, Kyoto (JP); Misa Tanaka, Matsue (JP); Hironori Kobayashi, Matsue (JP); Shunji Tomatsu, Wilmington, DE (US)

(73) Assignees: SHIMADZU CORPORATION, Kyoto (JP); NATIONAL UNIVERSITY CORPORATION SHIMANE UNIVERSITY, Matsue (JP)

( * ) Notice: Subject to any disclaimer, the term of this patent is extended or adjusted under 35 U.S.C. 154(b) by 0 days.

(21) Appl. No.: 17/501,387

(22) Filed: Oct. 14, 2021

(65) Prior Publication Data
US 2023/0122509 A1    Apr. 20, 2023

(51) Int. Cl.
| G01N 33/50 | (2006.01) |
| G01N 30/72 | (2006.01) |
| G01N 33/68 | (2006.01) |

(52) U.S. Cl.
CPC ......... G01N 33/50 (2013.01); G01N 30/7233 (2013.01); G01N 33/6893 (2013.01);
(Continued)

(58) Field of Classification Search
CPC . G01N 33/50; G01N 30/7233; G01N 2400/40
See application file for complete search history.

(56) References Cited

U.S. PATENT DOCUMENTS

| 2007/0161074 A1 | 7/2007 | Tomatsu et al. |
| 2007/0232564 A1 | 10/2007 | Sugahara |

(Continued)

FOREIGN PATENT DOCUMENTS

| JP | 2008-102114 A | 5/2008 |
| JP | 2020173228 A * | 10/2020 |
| WO | 2005/103089 A1 | 11/2005 |

OTHER PUBLICATIONS

Hiroe, Y., et al. "The Retention Behavior of CAPCELL CORE ADME S2.7, a Novel Adamantyl Stationary Phase in the Reversed-Phase Chromatography of Polar Compounds." The Application Notebook (2016), pp. 22-23. Accessed Online Feb. 22, 2023. <tinyurl.com/2p8474uc>. (Year: 2016).*

(Continued)

*Primary Examiner* — Neil N Turk
(74) *Attorney, Agent, or Firm* — Sughrue Mion, PLLC

(57) ABSTRACT

Provided is a method by which the disaccharides derived from glycosaminoglycans can be analyzed in a stable and highly reproducible manner. A method for analyzing a glycosaminoglycan according to the present invention includes: a first process for producing a plurality of kinds of disaccharides derived from a glycosaminoglycan in a biological sample by adding a plurality of kinds of glycosaminoglycan-specific enzymes to the biological sample; and a second process for separating and analyzing the plurality of kinds of disaccharides by a liquid chromatography-mass spectrometry method, where a column used for liquid chromatography in the liquid chromatography-mass spectrometry method is a column packed with a stationary-phase support to which an amide group as a functional group is bound, or a column packed with a stationary-phase support to which an adamantyl group as a functional group is bound.

1 Claim, 4 Drawing Sheets

(52) U.S. Cl.
CPC ..... *G01N 2400/38* (2013.01); *G01N 2400/40* (2013.01); *G01N 2800/04* (2013.01)

(56) References Cited

U.S. PATENT DOCUMENTS

| | | |
|---|---|---|
| 2011/0008810 A1 | 1/2011 | Tomatsu et al. |
| 2012/0040333 A1* | 2/2012 | Landry .................. C12Q 1/527 435/4 |
| 2015/0247829 A1* | 9/2015 | Sumiyoshi .......... H01J 49/0031 250/288 |

OTHER PUBLICATIONS

Shunji Tomatsu et al., Establishment of Glycosaminoglycan Assays for Mucopolysaccharidoses, Metabolites, Aug. 11, 2014, pp. 655-679, vol. 4.

Office Action dated Aug. 9, 2022, issued in Japanese Application No. 2019-076685.

Yusuke Okamoto, "Comprehensive analysis of glycosaminoglycans derived from natural products and development of a simple analysis method thereof", Graduate School of Pharmaceutical Sciences, Chiba University, Dissertation, 2018, pp. 1-43 (88 pages).

Office Action dated Nov. 8, 2022 issued by the Japanese Patent Office in Japanese Application No. 2019-076685.

\* cited by examiner

METHOD FOR ANALYZING GLYCOSAMINOGLYCAN

TECHNICAL FIELD

The present invention relates to a method for analyzing glycosaminoglycans.

BACKGROUND ART

Glycosaminoglycans (hereinafter abbreviated as "GAGs") are linear polysaccharides having a structure in which disaccharides as building blocks are repeatedly arrayed, with each disaccharide composed of a hexosamine combined with either a uronic acid or galactose. GAGs are classified by the composition of the disaccharide, such as the hyaluronic acid, chondroitin sulfate, dermatan sulfate, keratan sulfate or heparan sulfate. GAGs are known as polysaccharides which exist in a protein-linked or non-linked form in cell membranes and extracellular matrices. Those substances have been drawing attention in biochemistry, biology, pharmacy, medicine and other related areas.

For example, mucopolysaccharidoses have been known as one of the diseases caused by a congenital disorder (reduced activity) or deficiency of an enzyme responsible for the catabolism of GAGs. In mucopolysaccharidoses, a specific GAG is accumulated in biological tissues, depending on the kind of disordered or deficient enzyme. Accordingly, it is possible to diagnose mucopolysaccharidoses by analyzing the kind of GAG contained in biological samples, such as blood samples.

In a conventionally used method for analyzing a GAG in a biological sample, the GAG is split into disaccharides by a splitting enzyme, which are subsequently separated by liquid chromatography and subjected to a measurement for determining absorbance, fluorescence intensity or other kinds of optical intensity. However, it has been difficult to simultaneously perform the measurement for a plurality of kinds of GAGs since disaccharides cannot be satisfactorily separated by liquid chromatography.

Patent Literature 1 and Non Patent Literature 1 disclose methods which enable a simultaneous measurement of a plurality of kinds of GAGs in a biological sample by using a liquid chromatography-mass spectrometry method. The method described in Patent Literature 1 uses a reversed phase column or Hypercarb® column as the column for liquid chromatography, while the method described in Non Patent Literature 1 uses a Hypercarb column.

CITATION LIST

Patent Literature

Patent Literature 1: JP 2008-102114 A

Non Patent Literature

Non Patent Literature 1: Shunji Tomatsu, et al., "Establishment of Glycosaminoglycan Assays for Mucopolysaccharidoses", *Metabolites* 2014, 4, 655-679; doi: 10.3390/metabo4030655

SUMMARY OF INVENTION

Technical Problem

Although the reversed phase column is a type of column commonly used in liquid chromatography, it has weak retention power for highly polar compounds, such as the disaccharides forming GAGs, so that it is difficult to perform a separative analysis in a stable manner. On the other hand, the Hypercarb column, which is a column packed with porous carbon-graphite cores, is characterized by its outstanding performance in the retention and separation of highly polar compounds. However, Hypercarb columns vary in retention, separation and other kinds of performance from one batch of products to another. Accordingly, the reproducibility of the analysis may become considerably low depending on the extent of the variation.

The problem to be solved by the present invention is to provide a method by which the disaccharides derived from glycosaminoglycans can be analyzed in a stable and highly reproducible manner.

Solution to Problem

The first mode of the method for analyzing a glycosaminoglycan according to the present invention developed for solving the previously described problem includes:
  a first process for producing a plurality of kinds of disaccharides derived from a glycosaminoglycan in a biological sample by adding a plurality of kinds of glycosaminoglycan-specific enzymes to the biological sample; and
  a second process for separating and analyzing the plurality of kinds of disaccharides by a liquid chromatography-mass spectrometry method,
  where a column used for liquid chromatography in the liquid chromatography-mass spectrometry method is a column packed with a stationary-phase support to which an amide group (carbamoyl group) as a functional group is bound.

The second mode of the method for analyzing a glycosaminoglycan according to the present invention developed for solving the previously described problem includes:
  a first process for producing a plurality of kinds of disaccharides derived from a glycosaminoglycan in a biological sample by adding a plurality of kinds of glycosaminoglycan-specific enzymes to the biological sample; and
  a second process for separating and analyzing the plurality of kinds of disaccharides by a liquid chromatography-mass spectrometry method,
  where a column used for liquid chromatography in the liquid chromatography-mass spectrometry method is a column packed with a stationary-phase support to which an adamantyl group as a functional group is bound.

Advantageous Effects of Invention

In the method for analyzing a glycosaminoglycan according to the present invention, a glycosaminoglycan in a biological sample is decomposed by an enzyme to produce a plurality of kinds of disaccharides. These disaccharides are subsequently separated and analyzed by a liquid chromatography-mass spectrometry method. Disaccharides forming a glycosaminoglycan are highly polar compounds which are strongly negative charged due to a large number of sulfate groups and carboxyl groups included in those compounds. In the present invention, a column packed with a stationary-phase support to which an amino group or adamantyl group, both of which are functional groups that strongly bind to highly polar compounds, is used for the liquid chromatography in the liquid chromatography mass spectrometry. This enables a stable and highly reproducible analysis of glycosaminoglycans.

DESCRIPTION OF EMBODIMENTS

Example

Figure 1:
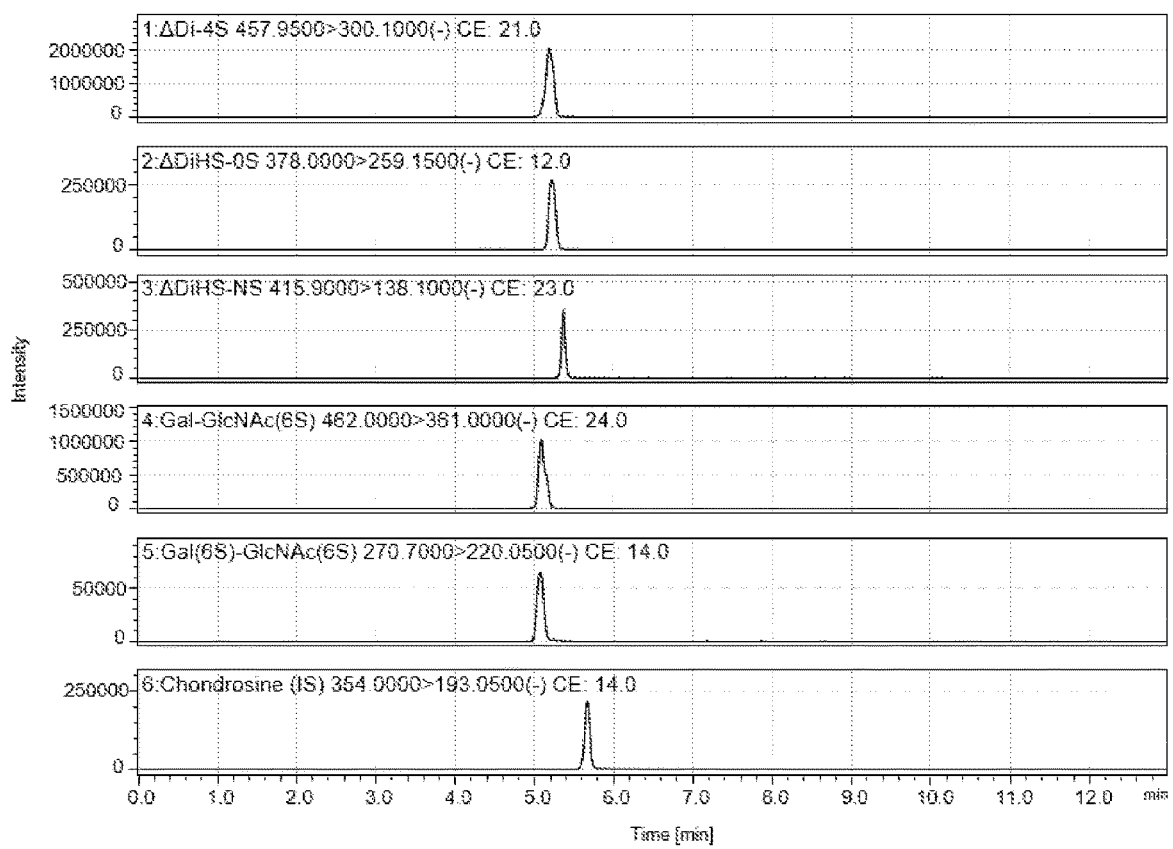
FIG. 1 shows MRM chromatograms obtained by LC/MS/MS analyses in which each of the combinations of the m/z of the precursor ion and that of the product ion specified for five kinds of disaccharides and one internal standard substance (chondrosine) was set as the MRM transition.

The present invention is hereinafter described in more detail based on specific examples. Those examples should not be interpreted as limitations of the present invention.

First Example

An experiment was initially conducted to determine where or not a glycosaminoglycan (GAG) m a biological sample can be analyzed by an MRM (multiple reaction monitoring) measurement using a liquid chromatograph mass spectrometer (LC/MS/MS).
<Sample Preparation>
A 1-µmol/L aqueous solution was prepared as a sample for the known compounds listed in Table 1 (including chondrosine as an internal standard substance for quantitative analysis). All compounds shown in Table 1 were purchased from Seikagaku Corporation.

TABLE 1

| | Compound Name | Origin |
|---|---|---|
| 1 | ΔDi-4S | CS, DS |
| 2 | ΔDi-0S | CS, DS |
| 3 | ΔDiHS-0S | HS |
| 4 | ΔDiHS-NS | HS |
| 5 | ΔDiHS-6S | HS |
| 6 | Gal-GlcNAc(6S) | KS |
| 7 | Gal(6S)-GlcNAc(6S) | KS |
| 8 | Chondrosine | Internal standard substance |

In Table 1, "CS", "DS", "HS" and "KS" are abbreviations for chondroitin sulfate, dermatan sulfate, heparan sulfate and keratan sulfate, respectively.

ΔDi-4S and ΔDi-0S are disaccharides resulting from the decomposition (digestion) of chondroitin sulfate and dermatan sulfate by chondroitinase B. ΔDiHS-0S, ΔDiHS-NS and ΔDiHS-6S are disaccharides resulting from the decomposition of heparan sulfate by heparitinase. Gal-GlcNAc(6S) and Gal(6S)-GlcNAc(6S) are disaccharides resulting from the decomposition of keratan sulfate by keratanase II.

The names of the devices and analysis conditions used for the liquid chromatography-mass spectrometry were as follows.
<Devices>
Liquid Chromatograph: Ultra High Performance Liquid Chromatograph Nexera X2 (manufactured by Shimadzu Corporation)
Mass Spectrometer: Ultra High Performance Triple Quadrupole Mass Spectrometer LCMS-8050 (manufactured by Shimadzu Corporation)
<LC Analysis Conditions>
Column: InertSustain® Amide column (GL Sciences Inc.), 2.1 mm I.D.×100 mm L, 3.0 µm
Mobile Phase: Mobile phase A, 5 mmol/L ammonium formate—acetonitrile
Mobile phase B, ammonium formate—ultrapure water
Gradient: B, concentration 5% by weight (0-1 min)→30% by weight (4 min)→90% by weight (5-8 min)→5% by weight (8.01-13 min)
Flow Rate: 0.3 mL/min
Column Temperature: 40 degrees Celsius
Injection Volume: 1 µL
<MS Analysis Conditions>
Ionization Mode: ESI (negative)
Analysis Mode: MRM
Nebulizer Gas Flow Rate: 3.0 L/min
Drying Gas Flow Rate: 10.0 mL % min
Interface Gas Flow Rate: 10.0 L/min
Interface Temperature: 300 degrees Celsius
Desolvation Line (DL) Temperature: 250 degrees Celsius
Heat Block Temperature: 400 degrees Celsius Table 2 shows the m/z of the precursor ion and that of the product ion (this combination is called the "MRM transition") as well as the collision energy (CE) for each disaccharide shown in Table 1, except for ΔDiHS-6S. The values in Table 2 were set taking into account the detection sensitivity for each disaccharide as well as the separation from other isobars. It should be noted that ΔDi-4S has the same precursor ion as ΔDiHS-6S and produces the same product ion (m/z 300.10) when subjected to mass spectrometry (MS/MS), so that it is impossible to separately detect these two compounds. Similarly, ΔDiHS-0S has the same precursor ion as ΔDi-0S and produces the same product ion (m/z 175.10) w % ben subjected to MS/MS, so that it is impossible to separately detect these two compounds.

TABLE 2

| | Compound Name | Precursor Ion (m/z) | Product Ion (m/z) | CE |
|---|---|---|---|---|
| 1 | ΔDi-4S | 457.95 | 300.10 | 21 |
| 2 | ΔDi-0S | 378.00 | 175.10 | 11 |
| 3 | ΔDiHS-0S | 378.00 | 259.15 | 12 |
| 4 | ΔDiHS-NS | 415.90 | 138.10 | 23 |
| 5 | Gal-GlcNAc(6S) | 462.00 | 361.00 | 24 |
| 6 | Gal(6S)-GlcNAc(6S) | 270.70 | 220.05 | 14 |
| 7 | Chondrosine | 354.00 | 193.05 | 14 |

The MRM chromatograms obtained by the LC/MS/MS analyses are shown in FIG. 1. The MRM chromatograms shown in FIG. 1 are the results of LC/MS/MS analyses in which each of the combinations of the m/z of the precursor ion and that of the product ion specified for ΔDi-4S, ΔDiHS-0S, ΔDiHS-NS, Gal-GlcNAc(6S), Gal(6S)-GlcNAc(6S) and chondrosine was set as the MRM transition from top to bottom. As shown in the topmost MRM chromatogram in FIG. 1, when the combination of the m/z of the precursor ion and that of the product ion specified for ΔDi-4S is set as the MRM transition, the peak of ΔDi-4S overlaps that of ΔDiHS-6S, so that the two compounds can neither be separated from each other in LC nor in MS. This means that ΔDi-4S and ΔDiHS-6S have substantially equal retention times in liquid chromatography.

When the components to be analyzed are a plurality of kinds of disaccharides that can neither be separated from each other in liquid chromatography nor in mass spectrometry as in the previous case, a plurality of samples for those disaccharides should be sequentially prepared from the same biological sample and subjected to the liquid chromatography-mass spectrometry, with one sample prepared by adding, to the biological sample, an enzyme that produces one of the disaccharides, another sample prepared by adding, to the biological sample, an enzyme that produces another one of the disaccharides, still another sample prepared by adding, to the biological sample, an enzyme that produces still another one of the disaccharides, and so on. In this manner, the plurality of kinds of disaccharides can be individually analyzed.

Second Example

An MRM measurement using the same LC/MS was performed for the same samples as in the first example, using a different type of column in the liquid chromatography for the LC/MS/MS. The conditions of the LC and MS analyses were as follows.
<LC Analysis Conditions>
  Column: CAPCELL PAK INERT ADME column (Osaka Soda Co., Ltd.), 2.0 mm I.D.×150 mm L, 3.0 μm
  Mobile Phase: Mobile phase A, 0.1% formic acid—ultrapure water
  Mobile phase B, 0.1% formic acid—acetonitrile
  Isocratic: B, concentration 2% by weight
  Flow Rate: 0.3 mL/min
  Column Temperature: 50 degrees Celsius
  Injection Volume: 1 μL
<MS Analysis Conditions>
  Ionization Mode: ESI (negative)
  Analysis Mode: MRM
  Nebulizer Gas Flow Rate: 3.0 L/min
  Drying Gas Flow Rate: 10.0 mL/min
  Heating Gas Flow Rate: 10.0 L/min
  Interface Temperature: 150 degrees Celsius
  Desolvation Line (DL) Temperature: 150 degrees Celsius
  Heat Block Temperature: 400 degrees Celsius
The conditions of the MRM measurement (MRM transitions and CEs) were the same as in the first example (Table 2).

Figure 2:
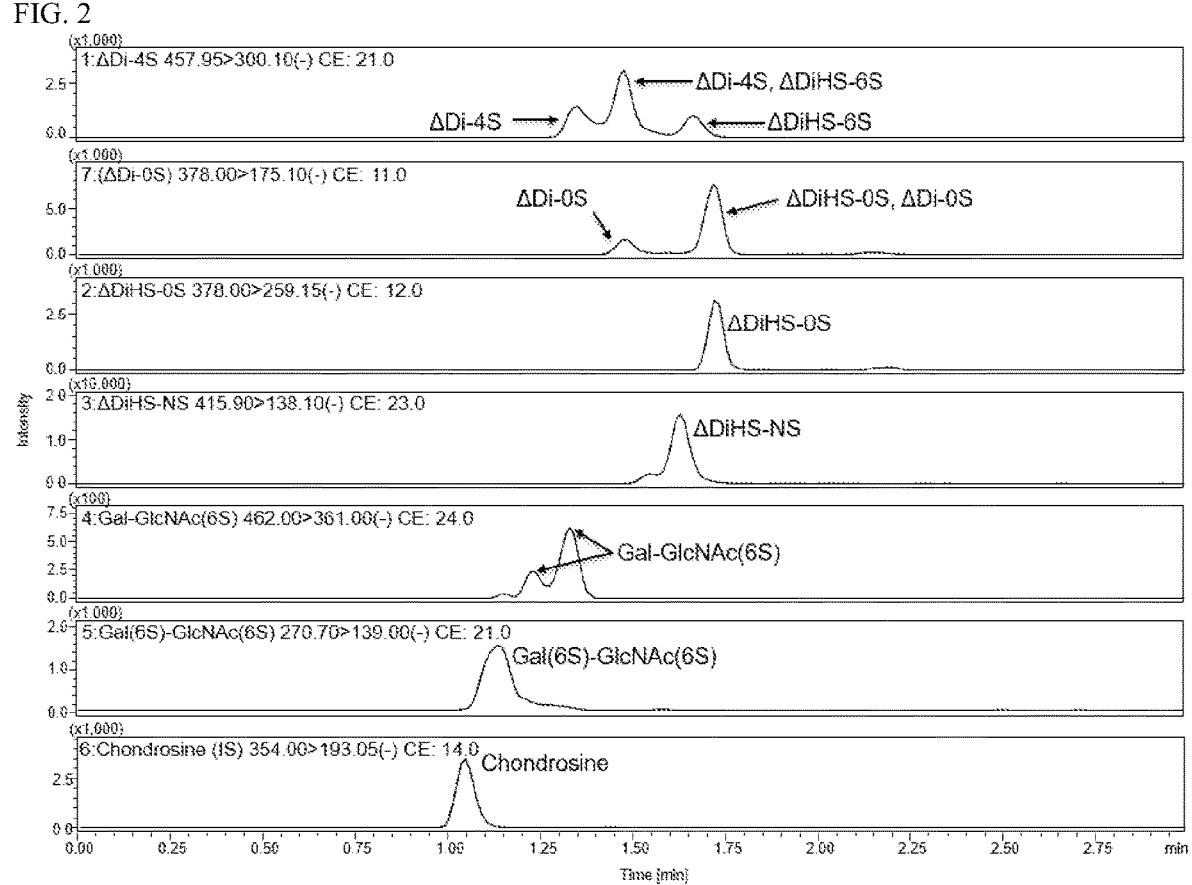
FIG. 2 shows MRM chromatograms obtained by LC/MS/MS analyses in which each of the combinations of the m/z of the precursor ion and that of the product ion specified for six kinds of disaccharides and one internal standard substance (chondrosine) was set as the MRM transition.

The MRM chromatograms obtained by the LC/MS/MS analyses are shown in FIG. 2. The MRM chromatograms shown in FIG. 2 are the results of LC/MS/MS analyses in which each of the combinations of the m/z of the precursor ion and that of the product ion specified for ΔDi-4S, ΔDi-0S, ΔDiHS-0S, ΔDiHS-NS, Gal-GlcNAc(6S), Gal(6S)-GlcNAc (6S) and chondrosine was set as the MRM transition from top to bottom. It should be noted that, as shown in FIG. 2, the peaks of ΔDi-4S and those of ΔDiHS-6S were observed in the topmost MRM chromatogram, while the peaks of ΔDi-0S and that of ΔDiHS-0S were observed in the second MRM chromatogram. Two peaks of Gal-GlcNAc(6S) were observed in the fifth MRM chromatogram.

A disaccharide having two peaks in one MRM chromatogram is most likely to have undergone anomer separation in the process of the liquid chromatography mass spectrometry. For example, the topmost MRM chromatogram in FIG. 2 has three peaks, of which the left peak and a portion of the central peak are the peaks of ΔDi-4S, while the right peak and a portion of the central peak are the peaks of ΔDiHS-6S. This means that both ΔDi-4S and ΔDiHS-6S underwent anomer separation, in which the retention time of one of the two anomers of ΔDi-4S which showed stronger retention was close to the retention time of one of the two anomers of ΔDiHS-6S which showed weaker retention, with the result that the two peaks overlapped each other and three peaks appeared in the MRM chromatogram. The second MRM chromatogram in FIG. 2 has two peaks, of which the left peak and a portion of the right peak are the peaks of ΔDi-0S, while a portion of the right peak is the peak of ΔDiHS-0S. This means that ΔDi-0S underwent anomer separation, in which the peak of the anomer which showed stronger retention overlapped the peak of ΔDiHS-0S, with the result that two peaks appeared in the MRM chromatogram.

A peak in which the peaks of a plurality of kinds of disaccharides overlap each other cannot be used for the quantitative determination of those disaccharides. In such a case, a peak which does not overlap any other disaccharide should be used for the quantitative determination of the disaccharide concerned. As a specific example, in the topmost MRM chromatogram in FIG. 2, the left peak with the shorter retention time should be used for the quantitative determination of ΔDi-4S, while the right peak with the longer retention time should be used for the quantitative determination of ΔDiHS-6S. The central peak should neither be used for the quantitative determination of ΔDi-4S nor ΔDiHS-6S.

Third Example

A mixed liquid of chondroitinase B, heparitinase and keratanase II, which are GAG-specific enzymes, was added to a blood sample (whole blood). A piece of filter paper was soaked in the blood sample and subsequently dried to obtain a dried-blood-spots (DBS) sample. Using the DBS sample as a biological sample, a recovered substance containing disaccharides extracted from the DBS sample was introduced into the LC/MS/MS to perform a quantitative analysis of the GAG. The LC analysis conditions, MS analysis conditions and MRM measurement conditions were identical to those used in the second example. For the present example, 10 DBS samples (DBS 1-10) were prepared. The procedure from the step of collecting the recovered substance from the DBS sample to the step of introducing the same substance into the LC/MS/MS was as follows.
<Collection of Disaccharides and Introduction into LC/MS/MS>
  1. The blood-soaked portion of each DBS sample was cut from the sample by a DBS puncher (PerkinElmer®, PerkinElmer Japan Co., Ltd.) to obtain a disk (3.3 mm in diameter).
  2. The disks were individually placed in the wells of a 96-well filter plate (Omega 10K, Pall Corporation), with each well containing 100 μL of 0.1% BSA.
  3. After the GAG-specific enzymes (chondroitinase B, heparitinase and keratanase II) were added to each well, the disks were incubated overnight at 37 degrees Celsius.
  4. The obtained GAG digests were filtered with the filter plate. The obtained filtrates were centrifuged at 2500×g for 15 minutes, and each of the recovered substances was introduced into the LC/MS/MS.

<Analysis Results>

Figure 3:
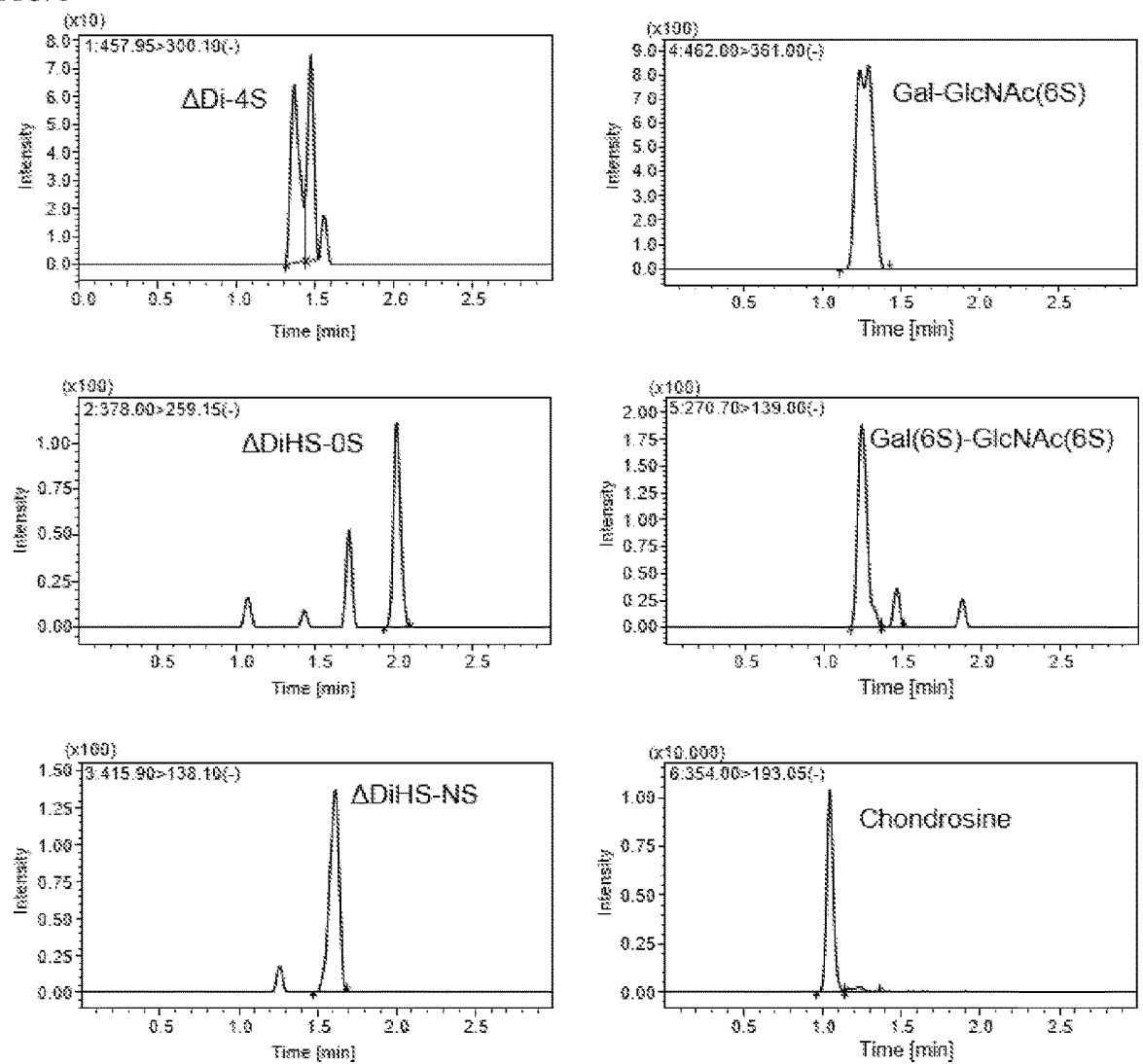
FIG. 3 shows MRM chromatograms obtained by analyzing a glycosaminoglycan in a blood sample (whole blood) by using a liquid chromatograph mass spectrometer.
Figure 4:
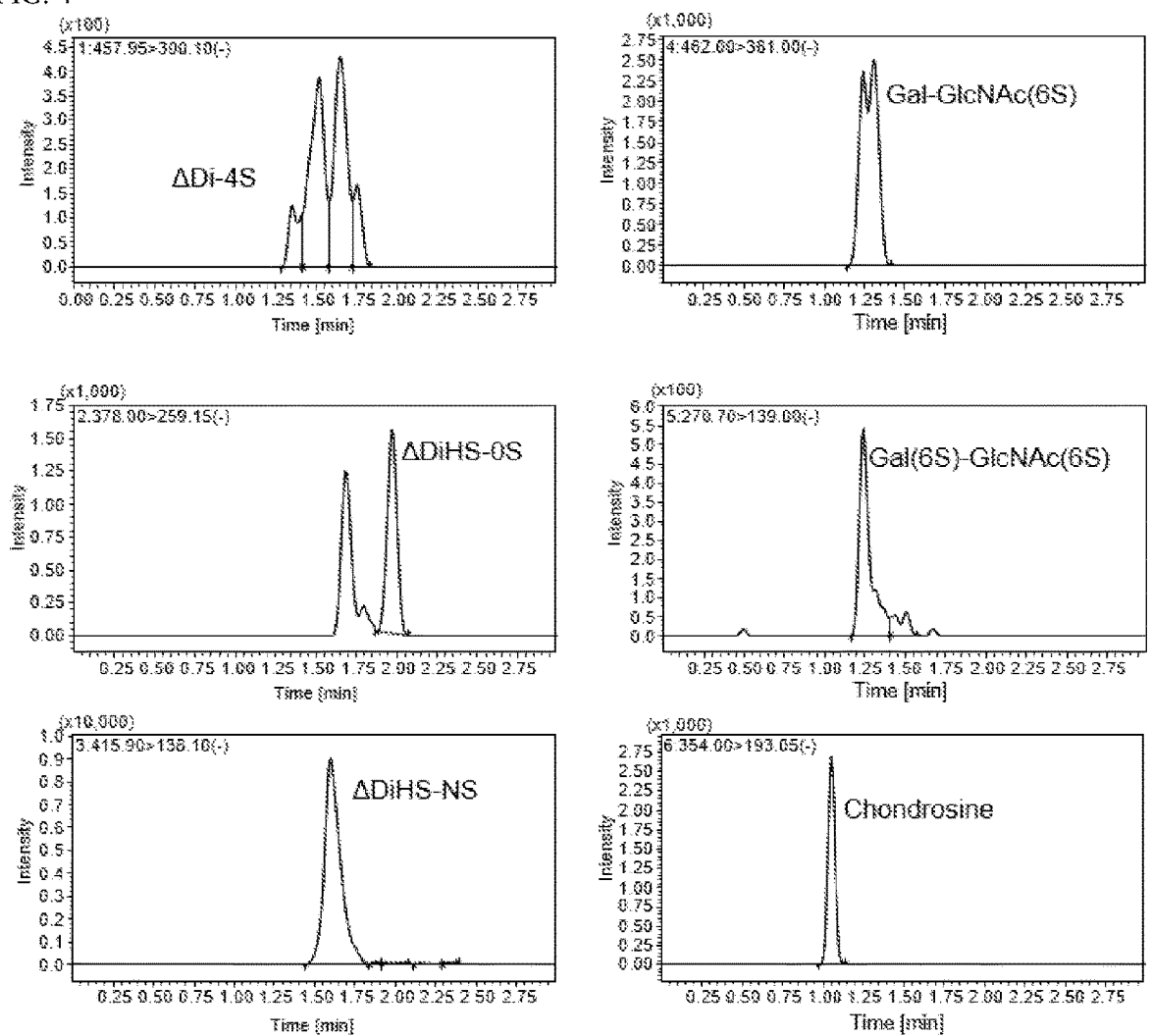
FIG. 4 shows MRM chromatograms obtained by analyzing a glycosaminoglycan in a blood sample (blood serum) by using a liquid chromatograph mass spectrometer.

The MRM chromatograms obtained by the LC/MS/MS analyses are shown in FIG. 3. The MRM chromatograms shown in FIG. 3 are the results of LC/MS/MS analyses in which each of the combinations of the m/z of the precursor ion and that of the product ion specified for ΔDi-4S, ΔDiHS-0S, ΔDiHS-NS, Gal-GlcNAc(6S) and Gal(6S)-GlcNAc(6S) and chondrosine was set as the MRM transition.

Table 3 shows the result of the quantitative determination of the disaccharides contained in each sample. The quantitative values were calculated by one-point calibration (internal standard method) using the result of an analysis for sample DBS4 to which 1 μmol/L of the solution of chondrosine shown in Table 2 (standard solution) was added.

TABLE 3

| | Concentration (nmol/L) | | | | |
|---|---|---|---|---|---|
| Sample | ΔDi-4S | ΔDiHS-0S | ΔDiHS-NS | Gal-GlcNAc(6S) | Gal(6S)-GlcNAc(6S) |
| DBS1 | — | 44.2 | 1.4 | 43.8 | 9.0 |
| DBS2 | — | — | 2.4 | 65.4 | 10.0 |
| DBS3 | — | 24.8 | 1.6 | 70.9 | 14.8 |
| DBS4 | — | — | 0.2 | 43.5 | 6.6 |
| DBS5 | 7.9 | 18.0 | 2.3 | 108.8 | 20.1 |
| DBS6 | — | 11.3 | 1.6 | 48.8 | 8.8 |
| DBS7 | — | 2.3 | 0.4 | 36.0 | 4.1 |
| DBS8 | — | 4.0 | 1.1 | 40.6 | 8.3 |
| DBS9 | — | 25.3 | 1.3 | 41.8 | 6.2 |
| DBS10 | — | 20.7 | 1.6 | 58.0 | 3.8 |

Table 4 shows the result of an investigation for an influence on the measurement of a matrix (foreign substance) contained in the samples. The influence of the matrix was calculated from the results obtained for (a) a sample consisting of sample DBS4 with 1 μmol/L of standard solution added, (b) 1 μmol/L of standard solution, and (c) sample DBS4.

TABLE 4

| Influence of Matrix (%) | | | | |
|---|---|---|---|---|
| ΔDi-4S | ΔDiHS-0S | ΔDiHS-NS | Gal-GlcNAc(6S) | Gal(6S)-GlcNAc(6S) |
| 115.1 | 65.3 | 93.2 | 124.4 | 135.6 |

Fourth Example

A mixed liquid of chondroitinase B, heparitinase and keratanase II, which are GAG-specific enzymes, was added to a blood (serum) sample. Using each serum sample as a biological sample, a recovered substance containing disaccharides extracted from the serum sample was introduced into the LC/MS/MS to perform a quantitative analysis of the GAG. The LC analysis conditions, MS analysis conditions and MRM measurement conditions were identical to those used in the second example. For the present example, 10 serum samples (Serum2, 4, 6, 8, 10, 12, 14, 16, 18, 20) were prepared. The procedure from the step of collecting the recovered substance from the serum sample to the step of introducing of the same substance into the LC/MS/MS was as follows.

<Collection of Disaccharides and Introduction into LC/MS/MS>

1. The serum samples (10 μL each) and a 50 mM tris-hydrochloric buffer solution (90 μL, pH 7.0) were put into the wells of a 96-well filter plate (Omega 10K, Pall Corporation).
2. The GAG-specific enzymes (chondroitinase B, heparitinase and keratanase 11) were added to each well. After the 50 mM tris-hydrochloric buffer solution (60 μL; pH 7.0) was further added to each well, the samples were incubated overnight at 37 degrees Celsius.
3. The samples held in the 96-well filter plate were centrifuged at 2200×g for 15 minutes, and each of the recovered substances was introduced into the LC/MS/MS.

<Analysis Results>

The MRM chromatograms obtained by the LC/MS/MS analyses are shown in FIG. 5. The MRM chromatograms shown in FIG. 5 are the results of LC/MS/MS analyses in which each of the combinations of the m/z of the precursor ion and that of the product ion specified for ΔDi-4S, ΔDiHS-0S, ΔDiHS-NS, Gal-GlcNAc(6S) and Gal(6S)-GlcNAc(6S) and chondrosine was set as the MRM transition.

Table 5 shows the result of the quantitative determination of the disaccharides contained in each sample. The quantitative values were calculated by one-point calibration (internal standard method) using the result of an analysis for serum sample Serum4 with 1 μmol/L of standard solution added.

TABLE 5

| | Concentration (nmol/L) | | | | |
|---|---|---|---|---|---|
| Sample | ΔDi-4S | ΔDiHS-0S | ΔDiHS-NS | Gal-GlcNAc(6S) | Gal(6S)-GlcNAc(6S) |
| Serum2 | 2.1 | — | 0.9 | 124.5 | 29.0 |
| Serum4 | — | 6.0 | 0.7 | 131.1 | 26.8 |
| Serum6 | — | 2.6 | 0.6 | 113.7 | 31.1 |
| Serum8 | — | 25.6 | 6.0 | 136.7 | 23.7 |
| Serum10 | — | 17.4 | 0.5 | 93.2 | 26.4 |
| Serum12 | — | 13.2 | 1.9 | 106.8 | 30.6 |
| Serum14 | — | 56.9 | 21.6 | 82.1 | 19.5 |
| Serum16 | — | 4.4 | 0.6 | 109.2 | 8.7 |
| Serum18 | 12.0 | 394.3 | 186.6 | 145.0 | 33.9 |
| Serum20 | — | 10.9 | 1.7 | 153.0 | 29.9 |

Table 6 shows the result of an investigation for an influence of the matrix. The influence of the matrix was calculated from the results obtained for (a) a sample consisting of serum sample Serum4 with 1 μmol/L of standard solution added, (b) 1 μmol/L of standard solution, and (c) serum sample Serum4.

TABLE 6

| Influence of Matrix (%) | | | | |
|---|---|---|---|---|
| ΔDi-4S | ΔDiHS-0S | ΔDiHS-NS | Gal-GlcNAc(6S) | Gal(6S)-GlcNAc(6S) |
| 129.8 | 127.6 | 122.7 | 162.4 | 190.0 |

An embodiment of the present invention has been described in detail. A person skilled in the art can understand that the previously described embodiment is a specific example of the following modes of the present invention.

The first mode of the present invention is an analysis method including:

a first process for producing a plurality of kinds of disaccharides derived from a glycosaminoglycan in a biological sample by adding a plurality of kinds of glycosaminoglycan-specific enzymes to the biological sample; and a second process for separating and analyzing the plurality of kinds of disaccharides by a liquid chromatography-mass spectrometry method, where a column used for liquid chromatography in the liquid chromatography-mass spectrometry method is a column packed with a stationary-phase support to which an amide group as a functional group is bound.

The second mode of the present invention is an analysis method including:

a first process for producing a plurality of kinds of disaccharides derived from a glycosaminoglycan in a biological sample by adding a plurality of kinds of glycosaminoglycan-specific enzymes to the biological sample; and a second process for separating and analyzing the plurality of kinds of disaccharides by a liquid chromatography-mass spectrometry method, where a column used for liquid chromatography in the liquid chromatography-mass spectrometry method is a column packed with a stationary-phase support to which an adamantyl group as a functional group is bound.

In the method for analyzing a glycosaminoglycan according to the first or second mode of the present invention, a column packed with a stationary-phase support to which an amide group or adamantyl group as a functional group is bound is used as the column for liquid chromatography in the liquid chromatography-mass spectrometry method. Both the amide group and adamantyl group can retain highly polar compounds, such as the disaccharides forming glycosaminoglycans, by a strong interaction with the highly polar compounds. Accordingly, glycosaminoglycans can be analyzed in a stable and highly reproducible manner.

The biological sample in the method for analyzing a glycosaminoglycan (which is hereinafter abbreviated as the "GAG") according to the first or second mode of the present invention may be any type of sample that contains a GAG and allows the GAG to be separated and analyzed by a liquid chromatography-mass spectrometry method. Specific examples include blood (whole blood, serum or plasma), urine, saliva, and biological tissues. Blood samples are preferable since they can be easily collected as biological samples, and they also contain a certain amount of GAG. Serum or plasma is particularly preferable.

The GAG-specific enzymes to be used in the method for analyzing a GAG according to the present invention may be any kinds of enzymes that specifically decompose GAGs. As for mucopolysaccharidoses, it is commonly known that keratan sulfate, heparan sulfate and dermatan sulfate are mainly accumulated in biological tissues. Accordingly, when a result obtained by the method for analyzing a GAG according to the present invention is used for the diagnosis of mucopolysaccharidoses, it is preferable to use enzymes which specifically decompose chondroitin sulfate, dermatan sulfate, keratan sulfate and heparan sulfate, respectively. The present invention allows two or more enzymes to be used in combination. Examples of the marketed products of the GAG-specific enzymes include keratanase, keratanase II, heparitinase, heparitinase I, heparitinase II, heparinase, and chondroitinase B.

As described earlier, in the first mode of the present invention, a column in which an amide group (carbamoyl group) as a functional group is bound to the stationary-phase support is used for liquid chromatography in the liquid chromatography-mass spectrometry method. An example of the marketed product of this type of column is the InertSustain® Amide analytical column (GL Sciences Inc.). This is a HILIC (hydrophilic interaction chromatography) type of column and is suitable for an analysis of polar compounds.

In the second mode of the present invention, a column in which an adamantyl group as a functional group is bound to the stationary-phase support is used for liquid chromatography in the liquid chromatography-mass spectrometry method. An example of the marketed product of this type of column is the CAPCELL PAK INERT ADME column (Osaka Soda Co., Ltd.). This is a reversed phase column and yet has a better balance between hydrophobicity and surface polarity on the surface of the stationary phase than conventional reversed phase columns, thereby enabling a stable separation of highly polar compounds.

In any of the first and second modes of the present invention, the period of time during which a disaccharide is retained within a column varies depending on the analysis conditions including the size (inner diameter and length) of the column, size of the stationary-phase support, nature (pH) of the mobile phase, flow rate of the mobile phase, and column temperature. Accordingly, in the present invention, the analysis conditions are appropriately set so that each disaccharide retained in the column will be eluted from the column after an appropriate period of time (retention time) for mass spectrometry.

In particular, in the methods for analyzing a glycosaminoglycan according to the first and second modes of the present invention, since a column in which a characteristic functional group is bound to the stationary-phase support is used as the column for liquid chromatography, the performance of the column for separating the disaccharides forming a glycosaminoglycan can be improved by selecting appropriate mobile phases.

In the third mode of the present invention, which is a specific form of the first mode of the method for analyzing a glycosaminoglycan, the first process includes (a) a process of adding, to the biological sample, a first enzyme which is one of the plurality of kinds of glycosaminoglycan-specific enzymes and produces at least one kind of disaccharide which is one of the plurality of kinds of disaccharides derived from the glycosaminoglycan in the biological sample, and (b) a process of adding, to the biological sample, a second enzyme which is one of the plurality of kinds of glycosaminoglycan-specific enzymes and produces one or more kinds of disaccharides derived from the glycosaminoglycan which are different from the disaccharide produced by the first enzyme, and the second process includes separately performing the liquid chromatography-mass spectrometry on a biological sample with the first enzyme added and a biological sample with the second enzyme added.

The third mode of the method for analyzing a glycosaminoglycan allows for an analysis of two kinds of saccharides which have substantially equal retention times in liquid chromatography as well as cannot be separately detected by mass spectrometry. Examples of such a combination of disaccharides include ΔDi-4S and ΔDiHS-6S as well as ΔDi-0S and ΔDiHS-0S.

In the fourth mode of the present invention, which is a specific form of the third mode of the method for analyzing a glycosaminoglycan, the disaccharide produced by the first enzyme includes ΔDi-4S w % bile the disaccharides produced by the second enzyme include ΔDiHS-6S, or the disaccharide produced by the first enzyme includes ΔDi-0S while the disaccharides produced by the second enzyme include ΔDiHS-0S.

In the fifth mode of the present invention, which is a specific form of the second mode of the method for analyzing a glycosaminoglycan, the second process includes using a peak having the shortest elution time or a peak having the longest elution time for quantitative determination of a disaccharide when an MRM chromatogram obtained as a result of the liquid chromatography-mass spectrometry for one MRM transition includes three or more peaks.

According to the fifth mode of the present invention, even when a disaccharide derived from the glycosaminoglycan by a glycosaminoglycan-specific enzyme has undergone anomer separation during the liquid chromatography-mass spectrometry, the quantitative analysis of the disaccharide can be satisfactorily performed.

A result obtained by the method for analyzing a glycosaminoglycan according to the first or second mode of the present invention can be used for testing for the presence or absence of mucopolysaccharidoses in a subject from which the biological sample has been collected. That is to say, another aspect of the first mode of the present invention is a method for testing for mucopolysaccharidoses, including:

a process of obtaining a biological sample from a subject;
a process of producing a plurality of kinds of disaccharides derived from a glycosaminoglycan in the biological sample by adding a plurality of kinds of glycosaminoglycan-specific enzymes to the biological sample;
a process of separating and analyzing the plurality of kinds of disaccharides by a liquid chromatography-mass spectrometry method; and
a process of testing for the presence or absence of mucopolysaccharidoses in the subject, based on a result of the analysis,
where a column used for liquid chromatography in the liquid chromatography-mass spectrometry method is a column packed with a stationary-phase support to which an amide group as a functional group is bound.

Additionally, another aspect of the second mode of the present invention is a method for testing for mucopolysaccharidoses, including:

a process of obtaining a biological sample from a subject;
a process of producing a plurality of kinds of disaccharides derived from a glycosaminoglycan in the biological sample by adding a plurality of kinds of glycosaminoglycan-specific enzymes to the biological sample;
a process of separating and analyzing the plurality of kinds of disaccharides by a liquid chromatography-mass spectrometry method; and
a process of testing for the presence or absence of mucopolysaccharidoses in the subject, based on a result of the analysis,
where a column used for liquid chromatography in the liquid chromatography-mass spectrometry method is a column packed with a stationary-phase support to which an adamantyl group as a functional group is bound.

The invention claimed is:

1. A method for analyzing a glycosaminoglycan, comprising:
a first process for producing a plurality of kinds of disaccharides derived from a glycosaminoglycan in a biological sample by adding a plurality of kinds of glycosaminoglycan-specific enzymes to the biological sample; and
a second process for separating and analyzing the plurality of kinds of disaccharides by a liquid chromatography-mass spectrometry method,
wherein a column used for liquid chromatography in the liquid chromatography-mass spectrometry method is a column packed with a stationary-phase support to which an adamantyl group as a functional group is bound, and
wherein when an MRM chromatogram obtained as a result of the liquid chromatography-mass spectrometry for the MRM transition of 457.95>300.10 contains three or more peaks, the second process includes detecting an amount of ΔDi-4S using a peak area value of a first peak with the shortest elution time and detecting an amount of ΔDi-6S using a peak area value of a second peak with the longest elution time.

* * * * *